(12) United States Patent
Seidel

(10) Patent No.: US 11,291,560 B2
(45) Date of Patent: Apr. 5, 2022

(54) ANTERIOR PORTAL ASSISTED TOTAL HIP ARTHROPLASTY

(71) Applicant: MicroPort Orthopedics Inc., Arlington, TN (US)

(72) Inventor: Matthew J. Seidel, Scottsdale, AZ (US)

(73) Assignee: MicroPort Orthopedics Inc., Arlington, TN (US)

(*) Notice: Subject to any disclaimer, the term of this patent is extended or adjusted under 35 U.S.C. 154(b) by 463 days.

(21) Appl. No.: 16/547,558

(22) Filed: Aug. 21, 2019

(65) Prior Publication Data
US 2020/0085589 A1    Mar. 19, 2020

Related U.S. Application Data

(60) Provisional application No. 62/721,135, filed on Aug. 22, 2018.

(51) Int. Cl.
| | |
|---|---|
| *A61F 2/46* | (2006.01) |
| *A61B 17/00* | (2006.01) |
| *A61F 2/36* | (2006.01) |
| *A61F 2/34* | (2006.01) |
| *A61B 17/56* | (2006.01) |

(52) U.S. Cl.
CPC ...... *A61F 2/4609* (2013.01); *A61B 17/00234* (2013.01); *A61B 2017/564* (2013.01); *A61F 2/34* (2013.01); *A61F 2/36* (2013.01); *A61F 2002/4635* (2013.01)

(58) Field of Classification Search
CPC .............. A61F 2/4609; A61B 17/1746; A61B 17/1739
See application file for complete search history.

(56) References Cited

U.S. PATENT DOCUMENTS

| | | | |
|---|---|---|---|
| 6,905,502 B2 * | 6/2005 | Penenberg | ......... A61B 17/1746 606/81 |
| 7,651,501 B2 * | 1/2010 | Penenberg | ....... A61B 17/00234 606/91 |

* cited by examiner

*Primary Examiner* — Andrew Yang
(74) *Attorney, Agent, or Firm* — Robert J. Hornung

(57) ABSTRACT

A method of total hip arthroplasty using a direct anterior approach to prepare an acetabulum of a patient for implantation of an acetabular cup implant, the method including providing a positioning instrument, forming a main incision substantially over the acetabulum, the main incision having a length of about the size the acetabular shell to be implanted, placing the positioning instrument in the main incision such that the shell of the positioning instrument rests in said acetabulum of the patient, and using a guide bore of the instrument to locate and form a portal incision, the portal incision communicating with the main incision. A cannula is inserted through the portal incision, such that a proximal end of the cannula extends from the portal incision and a distal end of the cannula is adjacent to and in communication with the acetabulum and main incision. The cannula is used to prepare the acetabulum and implant the final implant.

10 Claims, 4 Drawing Sheets

ANTERIOR PORTAL ASSISTED TOTAL HIP ARTHROPLASTY

STATEMENT REGARDING FEDERALLY SPONSORED RESEARCH

Not applicable

FIELD OF THE INVENTION

The present invention relates to total hip arthroplasty (THA), and more particularly to methods of performing total hip arthroplasty using an anterior approach.

BACKGROUND OF THE INVENTION

Over the years, a great deal of progress has been made in the field of total hip arthroplasty (THA), commonly known as hip replacement. In THA, the natural articulating surfaces of the hip joint are replaced with a femoral stem implant and an acetabular cup implant. Numerous instruments and techniques have been developed for preparing the femur and acetabulum to receive the implants. Approaches include anterior, anterolateral, lateral, posterolateral, posterior, and superior. Each of these approaches has advantages and disadvantages, most of which are dictated by the natural anatomy that is encountered when using the particular approach.

In conventional THA, it is common to make a relatively large incision, such as between 8 to 12 inches, in order to provide sufficient access to the joint and for the implantation of instruments. Large incisions may increase operating time and cause patients to lose large amounts of blood, suffer significant trauma to surrounding tissues (nerves and muscles), increase the risk of infection and require longer recovery periods.

In recent years, efforts have been made to develop "minimally invasive" procedures that reduce the incision length required for the particular approach, with the aim of reducing blood loss, trauma, risk of infection, and recovery time. However, small incisions also pose potential problems, such as small working space, longer operating time, and increased risk of poor implantation.

Efforts have been made to develop minimally invasive procedures for posterior approaches. See U.S. Pat. No. 6,905,502 (Brad Penenberg, M.D.) and its family members (U.S. Pat. Nos. 6,997,928, 7,833,229 and 6,997,928), each of which is incorporated herein by reference in its entirety. These patents describe the earliest efforts to use a portal incision in conjunction with a main incision in order to prepare the acetabulum for receipt of a hip implant using a posterior approach. Refinements of these instruments and methods are described in U.S. Pat. No. 7,651,501 (Brad Penenberg, M.D.) and its progeny (U.S. Pat. Nos. 8,439,928, 9,180,023, and 9,539,113), each of which is incorporated herein by reference in its entirety. In these methods, a specially configured guide is placed into the main incision. A portion of the guide is placed in the acetabulum to provide a reference point. An outrigger structure extends from the guide outside of the main incision. An outer portion of the outrigger includes a guide for guiding instruments such as trocars and cannulas into alignment with the acetabulum. The guide is used to form a small posterior portal incision in alignment with the acetabulum, as well as to hold a cannula and to guide instruments during preparation of the acetabulum. By using a small posterior portal incision in conjunction with a main incision, the length of the main incision can be reduced to about the size of the acetabular cup, such as 2 to 3 inches. Techniques for using the outrigger in a posterior approach are described in the foregoing patents.

While the foregoing techniques using portal and main incisions with outrigger instruments have been successful with posterior approaches to THA, up until now, efforts have not been made to adapt such techniques to a direct anterior approach. As will be described below, there are advantages to doing so. In a conventional direct anterior procedure, the incision is made anterior over the tensor facia lata lateral and distal to the anterior superior iliac spine and then directed distally for as long as necessary to provide a desired exposure. Alternatively, some direct anterior surgeons use what is known as a "bikini" skin incision centered over the same general location, roughly centered over the femoral head neck junction, but following the crease of the skin. Subcutaneous dissection is along the lateral side of the lateral femoral cutaneous nerve. The location and length of the direct anterior incision risks exposing and potentially injuring the lateral femoral cutaneous nerve (LFCN), the lateral femoral circumflex blood vessels, and the vastus lateralis muscle. The use of offset instrumentation in direct anterior procedures can reduce the length of the incision and the amount of tissue disruption, but visualization is reduced and the procedure is more complex than with straight acetabular instrumentation.

Additionally, anterior approaches have lower dislocation rates than traditional posterior approaches (about 1% versus 5%), which is believed to be due to the fact that the posterior capsule and the external rotators are left intact and the implant placement is carried out with visualization. An anterior approach also provides faster rehabilitation of patients than other approaches. More patients are discharged home after surgery, there is less use of assistive devices such as canes, and less pain medicine is required.

There is thus a need for the techniques described herein below, which enable a reduced incision, good visualization, the use of straight acetabular instruments, and other benefits that have heretofore not been obtained in direct anterior THA procedures.

OBJECTS AND SUMMARY OF THE INVENTION

It is an object of the invention to provide direct anterior approaches to total hip arthroplasty that maintain the minimal incision and soft tissue disruption possible with offset instrumentation while providing the visualization and simplicity of straight acetabular instrumentation.

It is another object of the invention to provide improved methods for anterior approaches to THA using a portal incision in minimally invasive hip procedures.

It is another object of the invention for providing a direct anterior approaches to THA that minimize the risk of damage to the lateral femoral cutaneous nerve, the lateral femoral circumflex vessels, and the vastus lateralis.

It is another object of the invention to provide direct anterior approaches to THA that achieve the minimal incision and soft tissue disruption possible with offset instrumentation while providing the visualization and simplicity of straight acetabular instrumentation.

The foregoing objectives are achieved by providing surgical techniques having the features described herein.

In embodiments, a method of total hip arthroplasty using a direct anterior approach to prepare an acetabulum of a patient for implantation of an acetabular cup implant in the patient is provided. The method comprises providing a positioning instrument. The positioning instrument comprises a main body portion having a handle on one end and an angled shell on an opposing end, the shell having a central axis, an outrigger arm extending from the main body adjacent the handle, the outrigger arm comprising a first arm portion that extends generally perpendicular to the main body portion, and a second arm portion that angles downward toward the main body portion, and a guide portion on an end of the second arm portion, the guide portion having a guide bore therethrough, an axis of the guide bore substantially aligned with the central axis of the shell. The method comprises determining a size of an acetabular shell implant to be implanted in the patient, forming an anterior main incision substantially over the acetabulum of the patient, the anterior main incision having a length of about the size of the acetabular shell to be implanted, placing the positioning instrument in the anterior main incision such that the shell of the positioning instrument rests in the acetabulum of the patient, using the guide bore of the guide ring to determine the location of an anterior portal incision, the location of the anterior portal incision distal to the anterior main incision by a distance sufficient to facilitate the use of straight-line instruments, forming the anterior portal incision at the determined location, inserting a cannula through the guide bore and into the anterior portal incision, a proximal end of the cannula extending from the anterior portal incision and a distal end of the cannula adjacent to and in communication with the acetabulum and the anterior main incision, removing the positioning instrument from the patient while retaining the cannula in the anterior portal incision, working a reaming instrument through the cannula to prepare the acetabulum for implantation of the acetabular shell implant, and working an impactor instrument through the cannula to implant the acetabular shell implant in the acetabulum.

In embodiments, the anterior main incision has a length of between about 2 and about 3 inches. In embodiments, the anterior portal incision has a length of between about 0.5 inches and about 1.0 inch. In embodiments, the anterior main incision begins about 3 to 5 cm lateral and about 3 cm distal from an anterior superior iliac spine of the patient and extends distally. The anterior main incision and the anterior portal incision can be formed through the tensor facia lata. The anterior main incision can be a bikini incision.

In embodiments, the reaming instrument and the impactor instrument are straight-line instruments. The lateral femoral cutaneous nerve, lateral femoral circumflex blood vessels, and vastus lateralis muscle of the patient are not exposed. A posterior capsule and external rotators of the patient are left intact.

The foregoing and other objects, features, aspects and advantages of the invention will become more apparent from the following detailed description of the invention when considered in conjunction with the accompanying drawings.

DETAILED DESCRIPTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
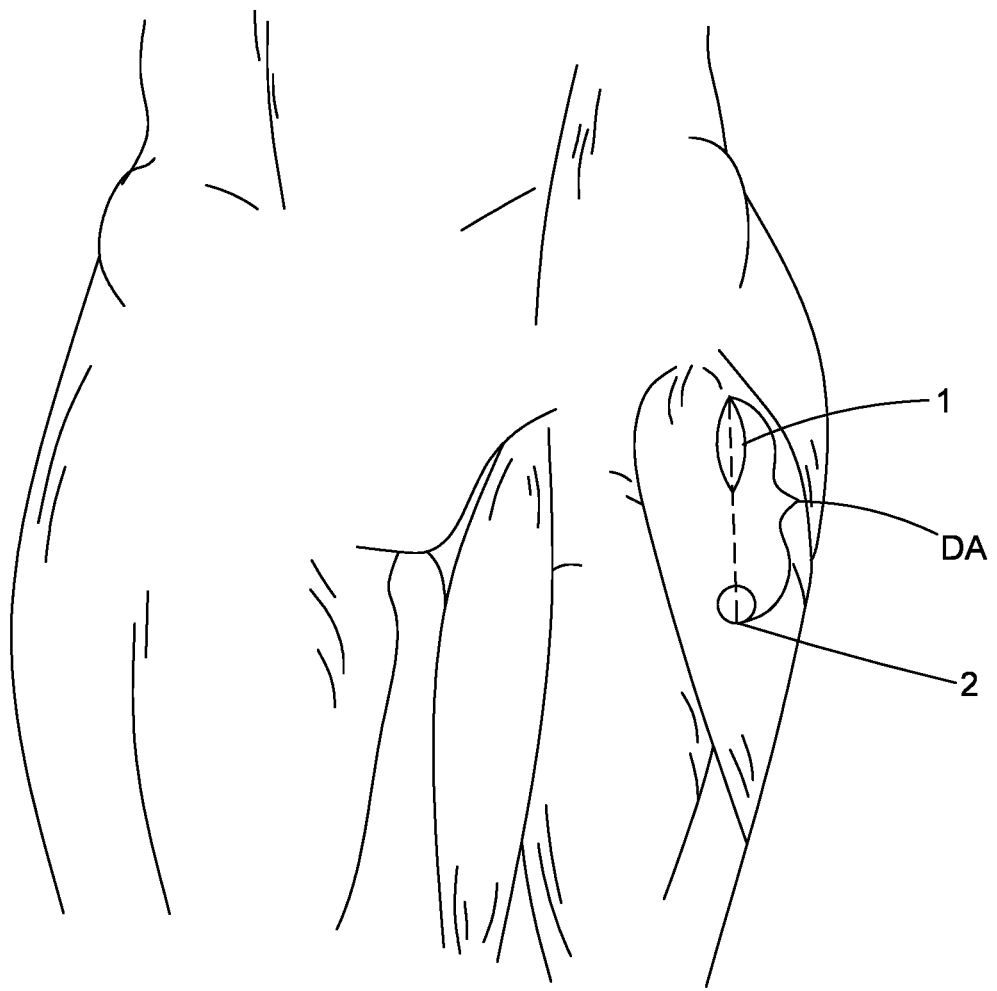
FIG. 1 shows a comparison between a conventional direct anterior incision and incisions used in a method of the invention.

As in a conventional direct anterior THA procedure, the patient is positioned supine on the operating table. FIG. 1 shows a comparison between the location of the incision DA (depicted by a dashed line) in a conventional direct anterior procedure and the location of the primary 1 and portal 2 incisions according to the procedure of the invention. As can be seen in FIG. 1, the conventional direct anterior incision DA is made anterior over the tensor facia lata (TFL) lateral and distal to the anterior superior iliac spine and then is directed distally for about 8 to 10 cm (3 to 4 inches) or as long as necessary to provide a desired exposure to the acetabulum. With the conventional direct anterior incision DA, the additional length is necessary in order to facilitate the use of straight reamer handles and cup impactors during preparation of the acetabulum and impaction of the cup. The alternative "bikini" incision is generally transverse to the conventional direct anterior skin incision, and would be centered over the shorter, proximally biased conventional incision.

Figure 2:
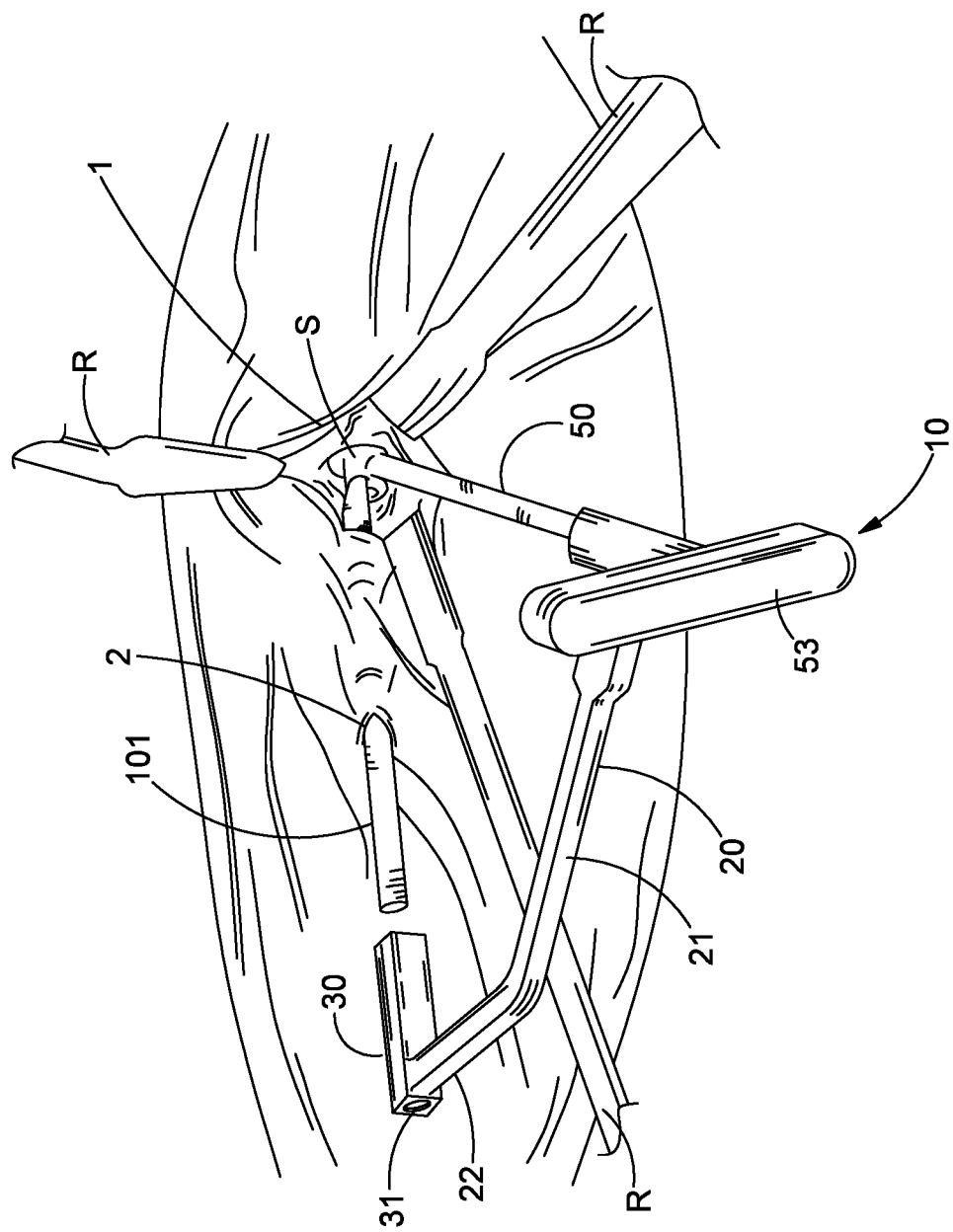
FIG. 2 shows use of a positioning instrument in a method of the invention.

As indicated in FIGS. 1 and 2, the procedure of the invention uses similar incision locations as a conventional direct anterior THA but significantly optimizes the position of and shortens the length of the main incision 1 through the use of a secondary portal incision 2. The shorter anterior main incision 1 is enabled by the use of a lengthwise internal portal formed through an anterior portal incision 2. The internal portal communicates between the portal incision 2 and the main incision 1. As can be seen in FIG. 1, the location of the portal incision 2 corresponds generally to the distal end of the conventional direct anterior incision DA that would normally be required in order to facilitate the use of straight reamer handles and cup impactors in the direct anterior approach THA.

The procedure begins with the formation of the main incision 1, followed by dissection to access the acetabulum. FIG. 2 shows a conventional direct anterior exposure with the main incision 1 under the waistline and centered above the femoral head. The main incision 1 begins roughly 3-5 cm lateral and 3 cm distal from the anterior superior iliac spine. The main incision 1 runs over the muscle belly of the tensor fascia lata (TFL). The main incision 1 is roughly the length of the acetabular shell S, the size of which has been determined by templating. The length of the main incisions 1 is typically between about 2 to about 3 inches (about 5 to 7 cm). The surgeon dissects through superficial fat to reach the thin facia over the muscle belly of the tensor fascia lata. The surgeon splits the fascia in-line with the tensor facia lata muscle fibers. A Smith-Peterson interval is developed until the capsule is reached. The branches of the lateral circumflex vessels are cauterized or ligated. Fat is excised over the capsule. A pair of retractors R are placed on either side of the femoral neck. The fibers of the rectus femoris are dissected medially from the capsule. A third retractor R is placed on the rim of the acetabulum and is used to retract the rectus tendon medially. The surgeon performs either a capsulotomy or a capsulectomy. The retractors R around the femoral neck are placed into the capsule. The femoral neck is cut and the femoral head is removed in the conventional manner. The retractors R are placed around the acetabulum for access and visualization. The labrum, fatty tissues and osteophytes are removed as needed.

Figure 3:
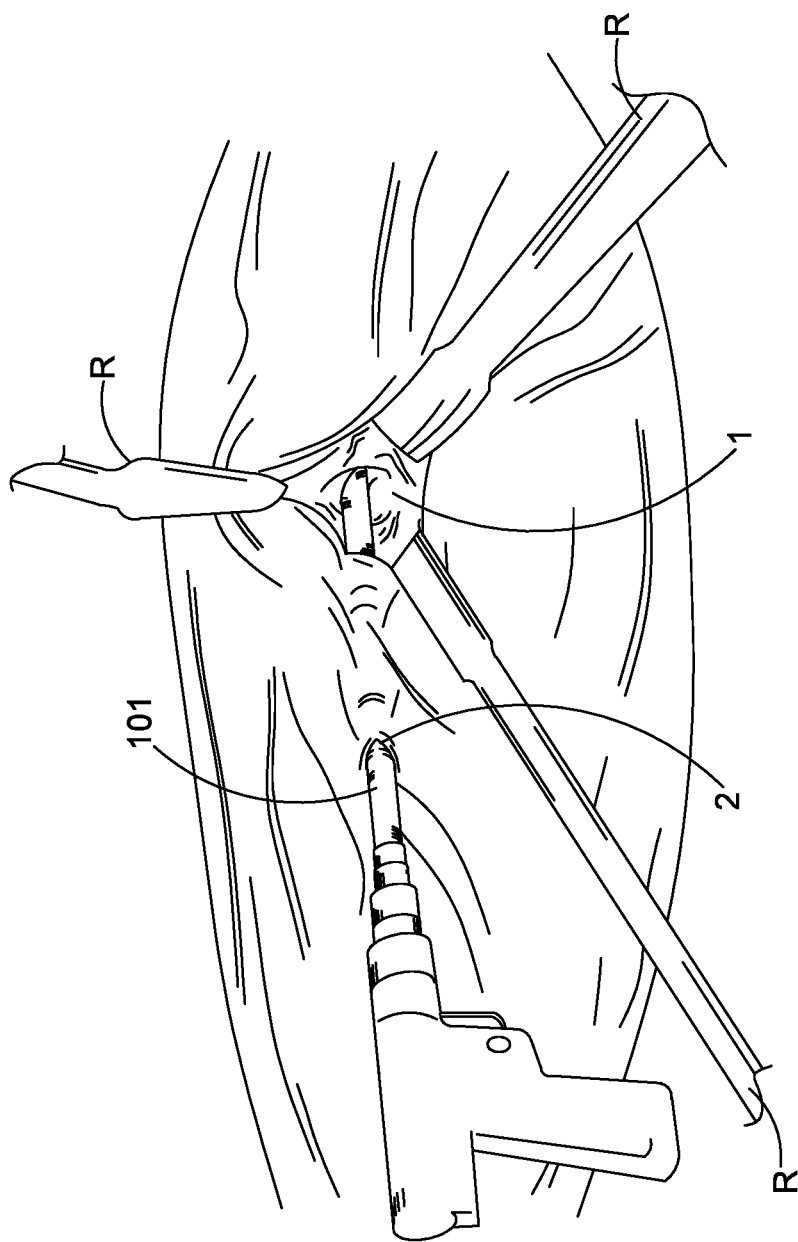
FIG. 3 shows an acetabular preparation step in a method of the invention.
Figure 4:
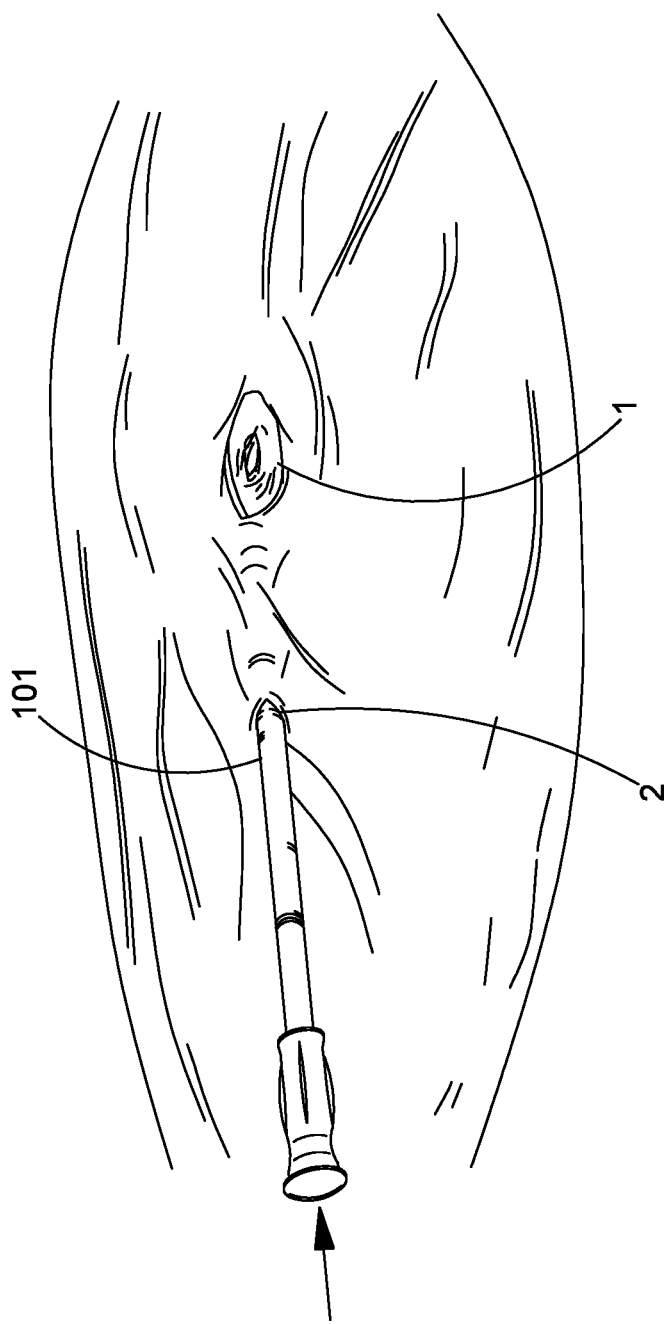
FIG. 4 shows an acetabular impaction step in a method of the invention.

Once access to the acetabulum has been established, the instrument 10 shown in FIGS. 2-4 is used to determination the location of the portal incision 2. Details about embodiments of positioning instruments suitable for use with the procedures of the invention are described in U.S. Pat. Nos. 7,651,501, 8,439,928, 9,180,023, and 9,539,113, which are incorporated herein by reference. The invention resides in the use of such instruments in a direct anterior procedure, which confers the benefits described herein. As indicated in FIG. 2, the positioning instrument 10 includes, generally, a main body portion 50 having a handle 53 on one end and an angled acetabular shell S on an opposing end. The shell S can be a trial shell or a shell implant. An outrigger arm 20 extends from the main body 50 adjacent the handle 53. The outrigger arm 20 comprises a first arm portion 21 that extends generally perpendicular to the main body portion 50, and a second arm portion 22 that angles downward toward the main body portion 50. An end of the second arm portion 22 is provided with a guide portion 30 that has a guide bore 31 therethrough. The positioning instrument 10 is configured such that an axis of the guide bore 31 substantially aligns with a central axis of the shell S.

In order to determine the location of the portal incision 2, the shell S of the positioning instrument 10 is passed through the main incision 1 and into contact with the patient's natural acetabulum. With the shell S positioned within the cup of the acetabulum, the surgeon positions the guide portion 30 of the instrument 10 so that it aligns with the main incision 1, at the location of the portal incision 2 indicated in FIG. 1. The location of the portal incision 2 can be marked according to the surgeon's preference. The portal incision 2 is made. The portal incision 2 is typically about 0.5 to 1.0 inches (about 1 to about 2.5 cm) in length.

A trocar (not shown) is inserted into the cannula 101 until a leading end of the trocar extends from the leading end of the cannula 101. The cannula 101 and trocar are inserted through the guide bore 31 of the guide portion 30. The trocar/cannula 101 are passed through the portal incision 2 and into communication with the acetabulum, using the guide portion 30 to maintain proper alignment relative to the shell S in the acetabulum. A cannula 101 is thus placed through the portal incision 2 anterior to the femur and generally collinear with the desired orientation of the acetabular shell component S. The intact skin and tissue between the main incision 1 and the percutaneous portal 2 placement represent the soft tissue that is spared using the technique of the invention.

In FIG. 2, the positioning instrument 10 is shown positioned in the main 1 and portal incisions 2 in the direct anterior approach of the invention. Once the cannula 101 is properly positioned, the trocar and instrument 10 are removed, leaving the cannula 101 in the portal incision, as shown in FIG. 3. As indicated in FIG. 3, the use of the cannula 101 in this manner allows for acetabular preparation through the cannula 101 under direct visualization though the main incision 1 above the resected femoral neck, with no instruments protruding from the main incision 1 other than soft tissue retractors R. As explained in the aforementioned U.S. Pat. Nos. 6,905,502, 6,997,928, 7,833,229 and 6,997,928 (Dr. Penenberg), which are incorporated herein by reference, a drive shaft is inserted through the cannula. Reamers are connected to a leading end of the drive shaft. A driver is used to drive the drive shaft to ream and prepare the acetabulum for receipt of an acetabular shell implant.

As shown in FIG. 4, the final implant is impacted through the cannula 101 and portal incision 2 under direct visualization and/or fluoroscopy without any instruments, including retractors R, in the main incision 1 impeding the ability of the surgeon to see the cup and acetabular landmarks directly.

If a shell and liner system is used, the shell is impacted through the cannula 101. At the surgeon's preference, screws can be used to secure the shell to the acetabulum. The screws can be introduced through the main incision 1, a screw driver can be passed through the cannula 101 located in the portal incision 2, and the screwdriver can be used to thread the screws into the bone of the acetabulum. The liner is then impacted into the shell through the cannula 101.

The femur is then prepared for receipt of a femoral stem and the remaining THA steps are carried out in the conventional manner.

Benefits of the method of the invention over conventional direct anterior THA will now be discussed. The use of a portal incision 2 decreases the risk of exposing and potentially injuring the lateral femoral cutaneous nerve (LFCN), lateral femoral circumflex vessels, and vastus lateralis.

The LFCN is a sensory nerve that travels under the skin of the leg starting from the anterior superior iliac spine (ASIS) and tracks laterally as it branches distally down the leg. The fact that the portal 2 allows the surgeon to avoid extending the incision distally, also means that the incision is less likely to expose or potentially injure the LFCN and maintain negligible risk of temporary lack of sensation of the outer thigh post-operatively.

The lateral femoral circumflex vessels supply blood to the femoral head, neck and greater trochanter. These vessels routinely travel through the distal portion of a traditional direct anterior incision, and are therefore compromised. The vessels are less likely to be damaged with the smaller incisions of the invention. This will improve bone health, which will in turn improve ingrowth of the femoral implant and reduce the risk of fracture.

The percutaneous portal 2 placement creates a small opening parallel to the muscle fibers. This avoids more extensive dissection and potential for incidental damage to the muscle by keeping the main incision 1 centered about the femoral head without the need for distal extension of the exposure.

The improved visualization through the main incision 1 decreases the amount of radiation exposure to the patient. Visualization is also improved by the smaller diameter of the instruments that pass through the portal 2, which results in less metal obstructing the fluoroscopic images that are created and used intra-operatively to confirm component placement. The reamer handles and cup impactors that pass through the portal incision 2 may be less than 1 cm in diameter.

The trajectory of the portal 2 also allows for in-line placement of acetabular screws without the need for flexible drills and drivers.

The anterior procedure of the invention also works well in high body mass index patients in comparison with a posterior approach, because fatty tissue does not obstruct the operative field. The anterior approach of the invention is also ideal for bilateral procedures, since both hips can easily be accessed with the patient in the supine position. Anterior approaches are also ideal for the use of fluoroscopy for intraoperative visualization for accurate component placement, including confirmation of implant size, confirmation of orientation, and confirmation of leg length. While the foregoing advantages are characteristic of anterior approaches in general, the use of a two incision approach enhances the advantages.

This method results in a direct anterior approach to total hip replacement that maintains the minimal incision and soft tissue disruption possible with offset instrumentation while providing the visualization and simplicity of straight acetabular instrumentation.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A method of total hip arthroplasty using a direct anterior approach to prepare an acetabulum of a patient for implantation of an acetabular cup implant in said patient, comprising:
   providing a positioning instrument, the positioning instrument comprising
      a main body portion having a handle on one end and an angled shell on an opposing end, the shell having a central axis,
      an outrigger arm extending from the main body adjacent the handle, the outrigger arm comprising a first arm portion that extends generally perpendicular to the main body portion, and a second arm portion that angles downward toward the main body portion, and
      a guide portion on an end of the second arm portion, the guide portion having a guide bore therethrough, an axis of the guide bore substantially aligned with the central axis of the shell,
   determining a size of an acetabular shell implant to be implanted in said patient,
   forming an anterior main incision substantially over said acetabulum of said patient, the anterior main incision having a length of about the size of the acetabular shell to be implanted,
   placing the positioning instrument in the anterior main incision such that the shell of the positioning instrument rests in said acetabulum of the patient,
   using the guide bore of the guide ring to determine the location of an anterior portal incision, the location of the anterior portal incision distal to the anterior main incision by a distance sufficient to facilitate the use of straight-line instruments,
   forming the anterior portal incision at the determined location,
   inserting a cannula through the guide bore and into the anterior portal incision, a proximal end of the cannula extending from the anterior portal incision and a distal end of the cannula adjacent to and in communication with said acetabulum and said anterior main incision,
   removing the positioning instrument from said patient while retaining the cannula in the anterior portal incision,
   working a reaming instrument through the cannula to prepare said acetabulum for implantation of the acetabular shell implant, and
   working an impactor instrument through the cannula to implant the acetabular shell implant in said acetabulum.

2. The method of claim 1, wherein the anterior main incision has a length of between about 2 and about 3 inches.

3. The method of claim 2, wherein the anterior portal incision has a length of between about 0.5 inches and about 1.0 inch.

4. The method of claim 1, wherein the anterior main incision begins about 3 to 5 cm lateral and about 3 cm distal from an anterior superior iliac spine of said patient and extends distally.

5. The method of claim 1, wherein the anterior main incision and the anterior portal incision are formed through the tensor facia lata.

6. The method of claim 1, wherein the anterior main incision is a bikini incision.

7. The method of claim 1, wherein the reaming instrument and the impactor instrument are straight-line instruments.

8. The method of claim 7, wherein a lateral femoral cutaneous nerve, lateral femoral circumflex blood vessels, and a vastus lateralis muscle of said patient are not exposed.

9. The method of claim 8, wherein a posterior capsule and external rotators of said patient are left intact.

10. The method of claim 1, wherein the guide bore is used to form the anterior portal incision.

* * * * *